United States Patent [19]

Haecker et al.

[11] 4,283,441

[45] Aug. 11, 1981

[54] METHOD OF MAKING AN ION CONDUCTIVE GAS SENSOR BODY WITH A CERMET ELECTRODE THEREON

[75] Inventors: Wolf-Dieter Haecker, Asperg; Karl-Hermann Friese, Leonberg, both of Fed. Rep. of Germany

[73] Assignee: Robert Bosch GmbH, Stuttgart, Fed. Rep. of Germany

[21] Appl. No.: 98,708

[22] Filed: Nov. 29, 1979

[30] Foreign Application Priority Data

Dec. 6, 1978 [DE] Fed. Rep. of Germany ....... 2852638

[51] Int. Cl.³ ............................................... B05D 5/12
[52] U.S. Cl. ............................ 427/126.2; 427/126.3; 427/126.5; 204/195 S
[58] Field of Search ............ 60/276; 427/126.2, 126.3, 427/126.5, 125, 376.3; 204/1 S, 195 S; 429/193; 106/57

[56] References Cited

U.S. PATENT DOCUMENTS

| | | | |
|---|---|---|---|
| 3,978,006 | 8/1976 | Topp et al. | 204/195 S X |
| 4,170,530 | 10/1979 | Watanabe et al. | 427/126.3 X |
| 4,209,377 | 6/1980 | Schinohara et al. | 204/195 S |
| 4,209,378 | 6/1980 | Schinohara et al. | 204/195 S |
| 4,221,650 | 9/1980 | Friese et al. | 204/195 S |

*Primary Examiner*—John D. Smith
*Assistant Examiner*—Bernard F. Plantz
*Attorney, Agent, or Firm*—Frishauf, Holtz, Goodman & Woodward

[57] ABSTRACT

To increase the response speed and sensitivity, while providing higher output voltages and permitting higher loading of the electrodes of gas sensors, particularly exhaust gas sensors to determine the transition of exhaust gases from internal combustion engines between reducing and oxidizing state, the sintering activity of the electrode which, typically, a cermet electrode, is selected to be less than that of the solid electrolyte body so that the resulting pore structure will be more open than that of the solid electrolyte body. The electrodes, essentially, consist of finely divided ceramic material, such as zirconium oxide, and finely divided electron conductive material such as platinum. On the pre-sintered solid electrolyte body, a mixture of the ceramic and the electron conductive material is applied in which the ceramic of the lattice support structure for the cermet electrode is less sinter-active than the ceramic of the solid electrolyte body, resulting in the improved pore structure of the cermet electrode layer.

11 Claims, 1 Drawing Figure

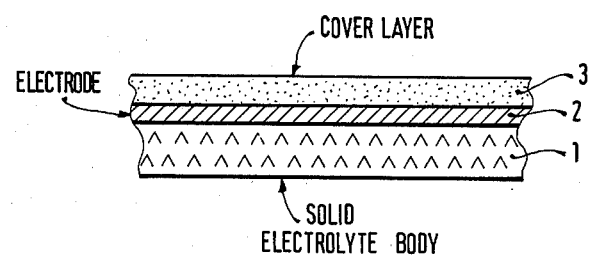

METHOD OF MAKING AN ION CONDUCTIVE GAS SENSOR BODY WITH A CERMET ELECTRODE THEREON

Reference to related patents and applications, assigned to the assignee of the present application:
U.S. Pat. No. 4,221,650, FRIESE et al;
U.S. Ser. No. 098,602, filed Nov. 29, 1979, Friese;
U.S. Ser. No. 100,256, filed Dec. 4, 1979, Maurer et al;

The present invention relates to gas sensors, and particularly to gas sensing elements to determine whether the exhaust gases from internal combustion engines are reducing or oxidizing. More specifically, the invention relates to a gas sensor of the type, for example, described in the referenced U.S. Pat. No. 3,978,006, Topp et al.

BACKGROUND AND PRIOR ART

The referenced U.S. Pat. No. 3,978,006 describes a gas sensor which has an ion conductive body on which an electrode layer is applied. This electrode layer is a mixture of a ceramic material and an electron conductive material, applied to the surface of the sensor. The layer of ceramic-ion conductive material and the electrolyte body are then, together, sintered. This method results in sensors eminently suitable to determine whether exhaust gases from internal combustion engines are reducing or oxidizing. When carrying out this process, particularly under mass production conditions, it is desirable to sinter the ceramic material applied to the surface of the sensor body together with sintering of the sensor body itself. The same ceramic material and the same sintering conditions are used. It has been found that sensors made in accordance with this process have a comparatively high electrode polarization, since the cermet electrodes which will result—that is, the ceramic-metal mixtures which form the electron conductive layer—will sinter to substantial density.

The sensors which indicate change in the gas composition as a voltage change can be loaded only lightly, that is, only small loading currents can be applied thereto without masking of the sensor signal itself. This requires, however, a complex sensing electronic network which is connected to the sensor itself in order to be able to distinguish between sensor signals and their characteristics, in dependence on the oxygen content of the gases to which the sensor is exposed. Such sensors are operative only at relatively high temperatures, since the internal resistance of the solid electrolyte body, due to the temperature dependence of the ion conduction, rises rapidly with decreasing temperature. The response sensitivity of such sensors is relatively low, that is, the time of reaction of sensor output with respect to change in the exhaust gas composition is relatively long, since the diffusion of gases through the densely sintered cermet electrode to the solid electrolyte body itself is impeded by the dense composition of the electrode.

Sensors which operate on the basis of current limits, and which indicate a change in the composition of the gases by change of the diffusion limiting current, have been proposed in which an artificial barrier, in form of a diffusion layer, is provided. Such sensors on the basis of current limits must have electrodes which can be loaded efficiently. The diffusion layer must have an acceptable low diffusion resistance in order to obtain current limit or threshold values which are unambiguously dependent on gas concentration. Diffusion layers with desirable diffusion resistance can be reproduced only with difficulty, particularly under mass production commercial conditions, and additionally reduce the sensitivity of the current limiting sensor and also increase its response time.

THE INVENTION

It is an object to provide a gas sensor which has a ceramic-metal electron conductive layer applied to an ion conductive body and which has rapid response time, high sensitivity, permits greater loading of the sensor, and still provides for good adhesion of the electron conductive layer to the underlying ion conductive body.

Briefly, the ceramic-metal electrode applied to the body has finely divided ceramic to form a support lattice for a finely divided conductive material and in which, according to the invention, the finely divided ceramic for the lattice comprises a material which has a lesser sintering activity than the sintering activity of the solid electrolyte, ion conductive body.

The ion conductive body and the ceramic material which forms the support lattice may consist, essentially, for example of zirconium dioxide, thorium oxide, hafnium oxide and/or cerium oxide; preferably, the ceramic material which forms the lattice support for the electron conductive metal has a higher component of stabilization additive, such as calcium oxide, $Y_2O_3$ or $Yb_2O_3$, than the zirconium oxide, or other material of the solid electrolyte body. The solid electrolyte body, preferably, contains at least partially stabilized zirconium oxide; the lattice support for the electron conductive material then preferably is completely stabilized zirconium oxide. Fluxes, such as silicates or sintering-enhancing materials and contaminants, such as titanium dioxide, $Al_2O_3$, phosphates, sulfates, or rare-earth oxides, may be present in the materials; in accordance with a feature of the invention, the material which forms the support lattice for the electron conductive metal contains a lesser quantity of such fluxes or contaminants than the ion conductive body. The electron conductive material may, for example, be platinum. Other metals are suitable, for example: rhodium, palladium or other metals of the platinum group of the periodic system of elements.

Drawing, illustrating an example, wherein the single FIGURE is a schematic cross-sectional view through a wall portion of a gas sensor which, in general, for example may have the structure shown in the aforementioned U.S. Pat. No. 3,978,006, Topp et al.

The lower sinter activity of the electron conductive layer, which forms the electrode, can be obtained in various ways. For example, the stabilization adddititive to the zirconium dioxide which forms the solid electrolyte ion conductive body—the preferred material used primarily in exhaust gas sensors—leads to a lower sintering activity. Ceramic components of zirconium dioxide which are mechanically stable and which have a sufficient $O^{2-}$ ion/conductivity must contain oxides such as CaO, $Y_2O_3$ in order to stabilize the cubic phase of the zirconium oxide, $ZrO_2$, (which is stable at high temperatures) also at lower temperatures. In many cases it is sufficient if the zirconium oxide is stabilized only partially in its cubic phase, that is, that the zirconium dioxide contains lesser quantities of stabilization oxide than is necessary for complete stabilization. Such partially stabilized zirconium oxide ceramic material may contain, for example, 5 mol-% $Y_2O_3$. If an electrode layer is applied to a sensor having such partially stabilized zirconium oxide, which has a ceramic content containing fully stabilized zirconium dioxide, for example containing 7.5 mol-% $Y_2O_3$ or $Yb_2O_3$ which is preferably already precalcined, the pore structure of the ceramic which will form at the electrode layer, due to the lesser sinter activity of such a ceramic, will be such that the desired higher loading and sensitivity of the sensor will be obtained. A further advantage of the use of completely stabilized zirconium oxide ceramic in the electron conductive layer is obtained due to increased ion conductivity in the range of the three phase boundaries due to the higher content of stabilizing oxides. A fully stabilized $ZrO_2$ ceramic which also contains $Al_2O_3$, can be used, since this ceramic has a particularly good temperature change stability (see referenced U.S. Pat. No. 4,221,650, FRIESE et al).

A further possibility to obtain zirconium oxide with a lower sinter activity is this: A lesser number of fluxes or contaminants which may lead to sintering are added to the zirconium oxide which forms the lattice structure for the electron conductive layer. Fluxes which are used in this art are, preferably, silicates such as kaolin, feldspar, nepheline-syenite or wollastonite. Sintering is enhanced by contaminants of the raw materials such as $TiO_2$, $Al_2O_3$, phosphates, sulfates, or oxides of rare earths. Fluxes are added to ceramic masses before sintering in order to obtain an especially dense structure. If the content of flux additives is less—assuming equal sintering conditions—then the cermet electrode will sinter to a less dense structure, which leads to a higher response sensitivity of the overall sensor.

A further possibility to make the ceramic of the electrode layer less sinter active can be achieved by grinding the raw materials for this layer somewhat less, or to start initially with coarser, and thus better crystallized, raw materials. An improved and more desirable pore structure is obtained which again leads to improved sensitivity. It is particularly desirable to use precalcined stabilized zirconium oxide powder only lightly ground as the raw material for the electron conductive layer.

Use of pure zirconium oxide without stabilizing additives as raw material for the support lattice of the electron conductive layer also leads to a desirable pore structure since the phase change in this case into $ZrO_2$, upon cooling, leads to fissures in the applied layer.

The cermet electrode can be so constructed that the portion facing the solid electrolyte body contains stabilized zirconium oxide and then there is applied thereover a layer of pure, unstabilized zirconium oxide to form the support lattice. Intermediate layers are obtained due to diffusion which result in an even better adhesion of the cermet electrode to the solid electrolyte body.

The Table, attached hereto and forming part of this specification, illustrates desirable characteristics of lattice structures for the cermet electrode and the results of use of various ones of such structures.

EXAMPLE 1

A solid electrolyte body of fully stabilized YSZ ceramic with 92.5 mol-% $ZrO_2$ and 7.5 mol-% $Y_2O_3$ with an additive of 30% $Al_2O_3$ (by weight) is shaped into the structure desired and pre-sintered for 2 hours at 1200° C. The cermet electrode is a suspension of 60 vol.-% platinum and 40 vol.-% CaO stabilized $ZrO_2$ powder.

Electrode composition: 1.45 parts (by weight) CSZ with 90 mol-% $ZrO_2$ and 10 mol-% CaO obtained from an arc melt are ground and sintered to a particle size of 2 to 10 $\mu m$. Added thereto are 2.2 parts (by weight) thinning oils, for example: oil of turpentine; 10.0 parts (by weight) commercial platinum suspension, consisting of: 70 w/o platinum and 30 w/o organic additives. The electrode material is ground in a centrifugal ball mill. The suspension is applied, as well known, by spraying, painting-on, rolling-on, dipping, pressure rolling, casting, or printing, for example screen printing, to have a layer thickness of from 10 to 30 $\mu m$. The sensor body with the layer thereon is then sintered in a gas-fired furnace at 1550° C. for about 5 hours.

EXAMPLE 2

Solid electrolyte body having fully stabilized CSZ ceramic with 85 mol-% $ZrO_2$ and 15 mol-% CaO and 3%, by weight, aluminum silicate, added in form of kaoline, and pre-sintered for 2 hours at 1100° C.

A platinum-cermet suspension, as in Example 1, is applied, with this change, however: The grain size of the CSZ powder is between 10 to 30 $\mu m$ and sintering is carried out in a gas-fired furnace at 1660° C. for about 5 hours.

EXAMPLE 3

Solid electrolyte body and other components as in Example 1, with this change: The cermet electrode, instead of CSZ powder, uses YSZ powder with 90 mol-% $ZrO_2$ and 10 mol-% $Y_2O_3$, calcined for 6 hours at 1600° C., and thereafter ground to a grain fraction of less than 50 $\mu m$.

EXAMPLE 4

Conditions as in Example 2, with this change: The CSZ raw material mixture is obtained from $ZrO_2$ powder and chalk powde., with a relative composition of 85 mol-% $ZrO_2$ and 15 mol-% CaO. No silicate additive.

EXAMPLE 5

Conditions and materials as in Example 1, with this change: Before sintering, a further platinum cermet layer is applied which consists of 60 vol.-% platinum and 40 vol.-% $ZrO_2$ powder, in which the $ZrO_2$ powder is ground to a specific surface of about 12 $m^2/g$.

EXAMPLE 6

Solid electrolyte consisting of partially stabilized YSZ ceramic of 95 mol-% $ZrO_2$ and 5 mol-% $Y_2O_3$ with an additive of 3% (by weight) $Al_2O_3$. The solid electrolyte body is pre-sintered for 2 hours at 1100° C.

The platinum suspension is constructed as in the above examples, with this change: The ceramic component uses an YSZ powder with a raw material mixture of 92.5 mol-% $ZrO_2$ and 7.5 mol-% $Y_2O_3$, to which 4% (by weight) $Al_2O_3$ are added. This mixture is ground dry to a specific surface of 11 $m^2/g$. Sintering at 1500° C. in a gas-fired furnace with a sintering time of about 5 hours.

The sensors made in accordance with any of the above examples are used, for example, to determine the transition of the composition of exhaust gases from reducing to oxidizing state. At the stoichiometric value, referred to as $\lambda = 1$, at 700° C., voltage changes of 300 mV/10 msec. are measured. In contrast, sensors in which the cermet electrodes have the same sintering activity as the solid electrolyte body show voltage changes of only 100 mV/10 msec.

The drawing shows a porous protective cover layer 3 over the sintered electrode 2 applied to sintered body 1.

TABLE

| Type of Solid Electrolyte Body | Preferred Support Lattice |
| --- | --- |
| Partially stabilized $ZrO_2$ (PSZ) (Sintering temperature 1400–1600° C.) | Fully stabilized $ZrO_2$ - raw material mixture or partially stabilized, pre-sintered lightly ground $ZrO_2$ powder |
| $Y_2O_3$ stabilized $ZrO_2$ (YSZ), fully stabilized (sintering temperature 1500–1650° C.) | fully stabilized, pre-calcined YSZ powder, possibly with an additive of pure $ZrO_2$ powder or CaO stabilized $ZrO_2$ (CSZ) |
| CaO stabilized $ZrO_2$ (CS) with flux additive (sintering temperature 1500–1700° C.) | CaO stabilized $ZrO_2$ (CSZ) without flux or with low flux additive content |

We claim:

1. In a method of making a cermet electrode for gas sensors having an ion conductive solid electrolyte body, in which the electrode essentially comprises a mixture of a finely divided ceramic to form a support lattice and a finely divided electron conductive material, and including the steps of applying the mixture of ceramic-electron conductive material to said body and sintering the body and mixture thereon to form a cermet electrode on the body, the improvement wherein
the finely divided ceramic for the lattice comprises a material having a lesser sintering activity than the sintering activity of the solid electrolyte body.

2. Method according to claim 1, wherein the ion conductive solid electrolyte body and the ceramic material forming the lattice for the electron conductive material comprises essentially a material selected from the group consisting of: zirconium dioxide, thorium oxide, hafnium oxide, cerium oxide.

3. Method according to claim 2, wherein the material of said group which forms the lattice structure has a higher content of stabilizing additive than the material of the group forming the solid electrolyte body;

and wherein the stabilizing additive comprises at least one of the materials of the group of: CaO, $Y_2O_3$ or $Yb_2O_3$.

4. Method according to claim 3, wherein the material of the solid electrolyte body comprises partially stabilized zirconium oxide, and the material for the lattice structure comprises fully stabilized zirconium oxide.

5. Method according to claim 4, wherein the zirconium oxide of the solid electrolyte body includes 5 mol-% $Y_2O_3$ and the zirconium oxide of the lattice structure includes 7.5 mol-% $Y_2O_3$.

6. Method according to claim 2, wherein flux additives are added to the material of said group;

and the material of the lattice support structure has a lesser content of flux additives than the material of the solid electrolyte body.

7. Method according to claim 6, wherein the flux additive comprises at least one of the materials of the group consisting of: silicate flux; sintering enhancing raw material contaminants selected from the group consisting of: titanium dioxide, $Al_2O_3$, phosphates, sulfates, or rare-earth oxides.

8. Method according to claim 1, wherein the materials of said group forming the lattice support structure are coarser than the raw materials for the solid electrolyte body.

9. Method according to claim 1, including the step of grinding the material of said group for pulverization thereof;

and where the grinding step of the material for the lattice structure is carried out to grind the material for the lattice structure to a lesser extent than the material for the solid electrolyte body.

10. Method according to claim 1, wherein said material for the lattice structure comprises pre-calcined, stabilized powder of a material selected from the group consisting of at least one of: $ZrO_2$, $ThO_2$, $HfO_2$, $CeO_2$.

11. Method according to claim 2, wherein the material for the lattice support structure comprises pure zirconium oxide without stabilization additive.

* * * * *